United States Patent [19]

Davis et al.

[11] 4,100,298

[45] Jul. 11, 1978

[54] DISPIROCYCLOPROPANE CARBOXYLATE PESTICIDES

[75] Inventors: Royston H. Davis; Robert J. G. Searle, both of Sittingbourne, England

[73] Assignee: Shell Oil Company, Houston, Tex.

[21] Appl. No.: 771,236

[22] Filed: Feb. 23, 1977

[30] Foreign Application Priority Data

Mar. 22, 1976 [GB] United Kingdom .............. 11440/76

[51] Int. Cl.$^2$ ...................... A01N 9/24; C07C 121/66; A01N 9/20

[52] U.S. Cl. ................. 424/304; 260/326 A; 260/326 N; 260/347.4; 260/465 D; 424/274; 424/285; 424/305; 560/102

[58] Field of Search ..................... 260/465 D; 424/304

[56] References Cited

U.S. PATENT DOCUMENTS

| | | | |
|---|---|---|---|
| 3,786,052 | 1/1974 | Martel et al. | 260/240 R |
| 3,950,535 | 4/1976 | Davis et al. | 424/304 |
| 3,979,424 | 9/1976 | Searle et al. | 260/465 D X |

*Primary Examiner*—Richard L. Raymond

[57] ABSTRACT

Certain dispirocyclopropane carboxylates are useful as pesticides.

8 Claims, No Drawings

DISPIROCYCLOPROPANE CARBOXYLATE PESTICIDES

FIELD OF THE INVENTION

This invention relates to novel dispirocyclopropane carboxylates which have useful pesticidal properties, especially insecticidal and acaricidal properties.

SUMMARY OF THE INVENTION

The present invention is directed to dispirocyclopropane carboxylate derivatives of the formula I

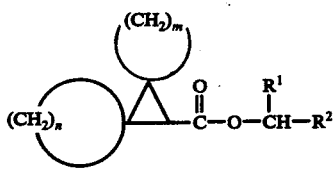

wherein $m$ and $n$ each independently represents an integer of from 2 to 5; $R^1$ represents a hydrogen atom, a cyano group or an alkynyl group of from 2 to 4 carbon atoms; and $R^2$ represents an optionally hydrogenated phthalimido group or a phenyl or furyl group substituted by phenoxy or benzyl.

Typical species within the scope of the invention include:

3-phenoxybenzyl dispiro(2.0.2.1)heptane-7-carboxylate

α-cyano-5-benzylfuranmethyl dispiro(2.0.5.1)decane-10-carboxylate

α-ethynyl-3,4,5-6-tetrahydrophthalimidomethyl dispiro(2.0.3.1)octane-8-carboxylate α-ethynyl-5-benzylfuranmethyl dispiro(2.0.3.1)octene-8-carboxylate α-cyano-phthalimidomethyl dispiro(2.0.3.1)octane-8-carboxylate α-cyano-3-benzylbenzyl dispiro(2.0.2.1)heptane-7-carboxylate α-ethynyl-5-phenoxyfuranmethyl dispiro(2.0.3.1)octane-8-carboxylate.

Preferred dispirocyclopropane carboxylate derivatives are those wherein $m$ is 2; $n$ is 3 or 4; $R^1$ represents a hydrogen atom, a cyano group or an ethynyl group and $R^2$ is a phenoxyphenyl or benzylfuryl group.

In general because of their insecticidal properties the derivatives of formula I wherein $R^1$ is a cyano group are preferred. For example, effective against Spodoptera littoralis larvae are α-cyano-3-phenoxybenzyl dispiro(2.0.3.1)octane-8-carboxylate and α-cyano-3-phenoxybenzyl dispiro(2.0.4.1)nonane-9-carboxylate. Variations in activity, of course, depend on the individual combinations of $m$, $n$, $R^1$ and $R^2$.

PREPARATION

The dispirocyclopropane derivatives of this invention may be prepared by a process which comprises reacting a compound of the formula:

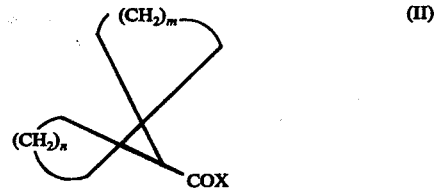

with a compound of formula:

wherein one of the groups X and Y represents a halogen, suitably chlorine or bromine, atom and the other represents a hydroxyl group; the other substituents having the meanings defined in formula I above. The reaction is conveniently carried out in the presence of a hydrogen halide acceptor, suitably a carbonate such as potassium carbonate, or a tertiary amine such as triethylamine, and in an organic solvent, such as diethylether or acetone.

The acid or acid halide of formula II may be prepared by appropriate adaptation of known procedures. One convenient synthesis route is to react a cycloalkanene with a triphenyl phosphonium cycloalkyl halide to form a dicycloalkene of formula:

which is then reacted with diazoacetic ester to form the ester of the desired dispiro acid, from which the free acid may be prepared by hydrolysis.

The dispirocyclopropane derivatives of the invention are of interest as pesticides, particularly as insecticides and acaricides for agricultural and domestic outlets. The invention therefore includes within its scope pesticidal compositions comprising a carrier and/or a surface-active agent together with, as active ingredient, a dispirocyclopropane carboxylic ester of formula I. Likewise the invention also includes a method of combating insect and/or acarid pests at a locus which comprises applying to the locus a pesticidally effective amount of a dispirocyclopropane carboxylic ester or composition of the invention.

The term 'carrier' as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomacious earths; magnesium silicates, for example, talcs, magnesium aluminium silicates, for example, attapulgites and vermiculites; aluminium silicates, for example, kaolinites, montmorillinites and micas; calcium carbonates; calcium sulphate; synthetic hydrated silicon oxides and synthetic calcium or aluminium silicates; elements such as for example, carbon and sulphur;

natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilisers, for example superphosphates.

Examples of suitable fluid carriers are water, alcohols, such as for example, isopropanol; glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine; light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides, fungicides, or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of etylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% w, preferably 0.5 to 75% w, of toxicant. Wettable powders are usually compounded to contain 25, 50 or 75% w of toxicant and usually contain, in addition to solid carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of toxicant. Granules are usually prepared to have a size between 10 and 100 BS mesh (1.676 – 0.152 mm), and may be manufactured by agglomeration or impregnation techniques. Generally, granules will contain ½–25% w toxicant and 0–10% w of additives such as stabilisers, slow release modifiers and binding agents. Emulsifiable concentrates usually contain, in addition to the solvent and, when necessary co-solvent, 10–50% w/v toxicant, 2–20% w/v emulsifiers and 0–20% w/v of appropriate additives such as stabilisers, penetrants and corrosion inhibitors. Suspension concentrates are compounded so as to obtain a stable, non-sedimenting, flowable product and usually contain 10–75% w toxicant, 0.5 – 15% w of dispersing agents, 0.1 – 10% w of suspending agents such as protective colloids and thixotropic agents, 0 – 10% w of appropriate additives such as defoamers, corrosion inhibitors, stabilisers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing pesticidal, for example insecticidal, acaricidal, herbicidal or fungicidal properties.

EXAMPLES

The invention is further illustrated in the following Examples which are provided for illustration only and should not be regarded as limiting the invention in any way.

EXAMPLE 1

3,4,5,6-Tetrahydrophthalimidomethyl dispiro(2.0.4.1.-)nonare-9-Carboxylate (A) Preparation of Dispiro(2.0.4.1.)nonan-9-carboxylic Acid Sodium hydride (50% dispersion in oil, 14.4g) was added over ¾ hour at 20° C to a mixture of triphenylphosphonium cyclopropyl bromide (prepared as described by J. Schweizer in J. Org. Chem. 1968 33 336; 114.1g) suspended in dry tetrahydrofuran (500 ml). Cyclopentanone (35.0g) was then added and the mixture refluxed for 1 hour, followed by distillation at atmospheric pressure to yield cyclopropylidene cyclopentane, b.pt. 132°–136° C.

Dry copper sulphate (0.1g) was added at 75° C to a solution of this product (1.8g) in petroleum ether (30ml), followed by dropwise addition of ethyl diazoacetate (15.0g). Chromatographic separation on a silica gel column using 2:1 hexane:chloroform as eluant yielded the ethyl ester of dispiro(2.0.4.1.)nonan-9-carboxylic acid, which was then stirred for 24 hours with potassium hydroxide (2.0g) in ethanol (20 ml) and water (20 ml), acidified and the product recrystallised from methanol/water to yield the free acid, m. pt. 83°–85° C.

Analysis : Calculated for $C_{10}H_{14}O_2$ C : 72.3; H 8.5%.
Found C : 71.9; H 8.5%.

(B) Dispiro(2.0.4.1.)nonan-9-carboxylate acid (0.66g) was converted to the corresponding acid chloride by refluxing with thionyl chloride (1 ml) in benzene (20 ml) for 1 hour. The acid chloride, N-hydroxymethyl-3,4,5,6-tetrahydrophthalimide (0.7g) and triethylamine (0.5g) were then stirred together in ether (50 ml) for 6 hours. After removal of solvent under reduced pressure the residue was purified by chromatography on silica gel using dichloromethane as eluant. The required product was obtained as an oil R.I. $n_D^{18}$ 1.5318.

Analysis : Calculated for $C_{19}H_{23}NO_4$ : C 69.3; H 7.0; N 4.2%.
Found : C 69.5; H 7.2; N 3.9%.

EXAMPLE 2 alpha-Cyano-3-phenoxybenzyl dispiro(2.0.3.1.)octane-8-carboxylate

Dispiro(2.0.3.1.)octane-8-carboxylic acid (0.75g), alpha-cyano-3-phenoxybenzyl bromide (1.4g) and potassium carbonate (0.7g) in acetone (50ml) were stirred together for 4 hours at 20° C. The mixture was filtered and the filtrate evaporated to give a pale yellow oil which was purified by chromatography on silica gel using a 1:1 mixture of dichloromethane and hexane as eluant. The required product was obtained as an oil R.I. $n_D^{19.5}$ 1.5572.

Analysis : Calculated for $C_{23}H_{21}NO_3$ : C 76.9; H 5.9; N 3.9%.

Found : C 77.3; H 6.1; N 3.5%.

EXAMPLES 3–6

Following procedures similar to those described in the foregoing Examples, further compounds according to the invention were prepared. The physical characteristics and analyses of these compounds are given in Table I.

III. In tests against glass house spider mites (*Tetranychus urticae*), leaf discs cut from French bean plants were sprayed in the manner described under II. 1 hour after spraying, the discs were inoculated with 10 adult mites. Mortality counts were made 24 hours after inoculation.

IV. The compounds were formulated as solutions or fine suspensions in water containing 20% by weight of acetone and 0.05% by weight of Triton D 100 as wetting agent. The formulations containing 0.6% by weight of Triton D 100 as wetting agent. The formulations contained 0.6% by weight of the compound to be tested. Pairs of leaves are removed from broad bean plants and placed on filter paper inside plastic petri dishes. Immediately prior to testing ten larvae of the Egyptian cotton leafworm (*Spodoptera littoralis*) are transferred onto the leaves and allowed to settle down. Larvae and leaves are sprayed together using a spraying machine delivering 340 liters/hectare, operated under the conveyor belt principle. After spraying the larvae are covered with a petri dish lid. After 24 hours, the percentage of dead and moribund larvae was recorded.

The results of these tests are shown in Table II in

TABLE I

| Example No. | Compound | R.I. of m.p. | Analysis | |
|---|---|---|---|---|
| 3 | alpha-Cyano-3-phenoxybenzyl, Dispiro (2.0.4.1)nonane-9-carboxylate | $n_D^{18.5}$ 1.5579 | Calculated for $C_{24}H_{23}NO_3$ Found | : C 77.2 ; H 6.2 ; N 3.7% : C 77.1 ; H 6.3 ; N 3.4% |
| 4 | alpha-Ethynyl-3-phenoxybenzyl Dispiro | $n_D^{19.0}$ 1.5636 | Calculated for $C_{25}H_{24}O_3$ Found | : C 80.6 ; H 6.5% : C 80.4 ; H 6.5% |
| 5 | 5-Benzylfuran-3-methyl Dispiro(2.0.4.1) nonane-9-carboxylate | $n_D^{17.5}$ 1.5424 | Calculated for $C_{22}H_{24}O_3$ Found | : C 78.5 ; H 7.2% : C 77.9 ; H 7.2% |
| 6 | Phthalimidomethyl Dispiro(2.0.4.1) nonane-9-carboxylate | m.p. 91–92° C | Calculated for $C_{19}H_{19}NO_4$ Found | : C 70.14 ; H 5.88 ; N 4.31% : C 70.20 ; H 6.0 ; N 4.2% |

EXAMPLE 7

Pesticidal Activity

The insecticidal and acaricidal activity of the compounds according to the present invention was tested as follows:

I. A 1.0% by weight solution in acetone of the compound to be tested was prepared, and taken up in a micrometer syringe. Two to 3-day old adult female house flies (*Musca domestica*) were anaesthetized with carbon dioxide, and 1 μl drop of the test solution was brushed off on the ventural abdomen of each, 20 flies being treated. The treated flies were held for 24 hours in glass jars, each containing a little granulated sugar as food for flies, and the percentage of dead and moribund individuals was then recorded.

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under-surface of the leaf with the above formulation. Spraying was effected with a spraying machine delivering 450 liters per hectare, the plants passing under the spray on a moving belt. Ten adult 1–2 week-old mustard beetles (*Phaedon cochleariae*) were placed on the spraying leaf of each turnip plant and ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours.

which the test species are identified by the initials noted above, and A denotes complete kill, B some kill C no kill of the test species.

TABLE II

| Compound of Ex. No. | Insecticidal Activity | | | | |
|---|---|---|---|---|---|
| | M.d. | P.c. | S.l. | M.v. | T.u. |
| 1 | C | A | C | A | C |
| 2 | A | C | A | A | B |
| 3 | A | B | A | B | C |
| 4 | A | C | A | A | C |
| 5 | A | A | C | B | A |

We claim:

1. A dispirocyclopropane carboxylate derivative of the formula

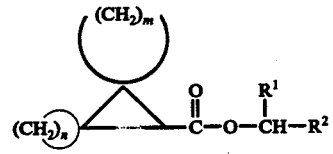

wherein $m$ and $n$ each independently represents an integer of from 2 to 5; $R^1$ represents a cyano group; and $R^2$ represents a phenyl group substituted by phenoxy or benzyl.

2. A dispirocyclopropane carboxylate derivative according to claim 1 wherein $m$ is 2 and $n$ is 3 or 4.

3. A dispirocyclopropane carboxylate derivative according to claim 2 wherein $R^2$ is phenoxyphenyl.

4. A dispirocyclopropane carboxylate derivative according to claim 3 wherein n is 3 and $R^2$ is 3-phenoxyphenyl.

5. A dispirocyclopropane carboxylate derivative according to claim 3 wherein n is 4 and $R^2$ is 3-phenoxyphenyl.

6. A method of combating insect or arachnid pests at a locus which comprises applying to the locus an insecticidally or acaricidally effective amount of a dispirocyclopropane carboxylate derivative according to claim 1 or a composition thereof.

7. A method according to claim 6 wherein the dispirocyclopropane carboxylate derivative is selected from α-cyano-3-phenoxybenzyl dispiro(2.0.3.1)octane-8-carboxylate or α-cyano-3-phenoxybenzyl dispiro(2.0.4.1)nonane-9-carboxylate.

8. An insecticidal or acaricidal composition comprising at least one carrier or surface active agent together with, as active agent, an effective amount of a dispirocyclopropane carboxylate derivative according to claim 1.

* * * * *